(12) United States Patent
Flohr et al.

(10) Patent No.: US 10,682,104 B2
(45) Date of Patent: Jun. 16, 2020

(54) COMPUTED TOMOGRAPHY RECORDING WITH DIFFERENT SETS OF ENERGY THRESHOLDS

(71) Applicant: Siemens Healthcare GmbH, Erlangen (DE)

(72) Inventors: Thomas Flohr, Uehfeld (DE); Michael Grasruck, Nuremberg (DE); Philipp Hoelzer, Baltimore, MD (US); Mark-Aleksi Keller-Reichenbecher, Sandhausen (DE); Bernhard Schmidt, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 205 days.

(21) Appl. No.: 16/050,093

(22) Filed: Jul. 31, 2018

(65) Prior Publication Data
US 2019/0038244 A1 Feb. 7, 2019

(30) Foreign Application Priority Data

Aug. 3, 2017 (DE) .................. 10 2017 213 479

(51) Int. Cl.
*A61B 6/03* (2006.01)
*A61B 6/00* (2006.01)
(Continued)

(52) U.S. Cl.
CPC ............ *A61B 6/4241* (2013.01); *A61B 6/032* (2013.01); *A61B 6/035* (2013.01); *A61B 6/06* (2013.01); *A61B 6/4035* (2013.01); *A61B 6/482* (2013.01); *A61B 6/5294* (2013.01); *A61B 6/54* (2013.01); *A61B 6/545* (2013.01); *G01N 23/046* (2013.01); *A61B 6/405* (2013.01); *A61B 6/503* (2013.01); *A61B 6/544* (2013.01)

(58) Field of Classification Search
None
See application file for complete search history.

(56) References Cited

U.S. PATENT DOCUMENTS

| | | | | |
|---|---|---|---|---|
| 7,260,174 B2 * | 8/2007 | Hoffman | ................ | A61B 6/032 250/363.09 |
| 7,570,736 B2 * | 8/2009 | Hoffman | ................ | A61B 6/032 378/19 |

(Continued)

FOREIGN PATENT DOCUMENTS

| | | |
|---|---|---|
| DE | 102007046514 A1 | 4/2009 |
| DE | 102015205301 A1 | 9/2016 |
| DE | 102015206630 A1 | 10/2016 |

*Primary Examiner* — Thomas R Artman
(74) *Attorney, Agent, or Firm* — Harness, Dickey & Pierce, P.L.C.

(57) ABSTRACT

A method is for recording a region of interest of an examination object with a computed tomography system including an energy-selective X-ray detector with a number of energy threshold values that can be set by way of an energy threshold values. In an embodiment, the method includes first recording of first projection scan data with a first set of energy thresholds; setting a second set of energy thresholds different from the first set of energy thresholds, based on a temporally variable parameter; and second recording of second projection scan data different from the first projection scan data with the second set of energy thresholds.

20 Claims, 2 Drawing Sheets

(51) Int. Cl.
*A61B 6/06* (2006.01)
*G01N 23/046* (2018.01)

(56) References Cited

U.S. PATENT DOCUMENTS

| | | | | |
|---|---|---|---|---|
| 7,583,790 | B2* | 9/2009 | Hoffman | A61B 6/032 250/370.09 |
| 7,606,347 | B2* | 10/2009 | Tkaczyk | A61B 6/032 378/19 |
| 7,634,060 | B2* | 12/2009 | Hoffman | A61B 6/032 250/370.09 |
| 7,697,659 | B2* | 4/2010 | Hoffman | A61B 6/032 378/19 |
| 8,068,578 | B2 | 11/2011 | Krauss | |
| 9,662,078 | B2* | 5/2017 | Berglund | A61B 6/4233 |
| 9,664,798 | B2* | 5/2017 | Kappler | G01T 1/17 |
| 9,861,324 | B2* | 1/2018 | Wang | A61B 6/482 |
| 10,548,543 | B2* | 2/2020 | Wang | A61B 6/4275 |
| 2006/0056581 | A1* | 3/2006 | Hoffman | A61B 6/032 378/19 |
| 2007/0140418 | A1* | 6/2007 | Hoffman | G01T 1/2928 378/19 |
| 2007/0206721 | A1* | 9/2007 | Tkaczyk | G01T 1/249 378/19 |
| 2007/0206722 | A1* | 9/2007 | Hoffman | A61B 6/5205 378/19 |
| 2007/0248209 | A1* | 10/2007 | Hoffman | A61B 6/4241 378/19 |
| 2008/0304618 | A1* | 12/2008 | Hoffman | A61B 6/032 378/5 |
| 2009/0086884 | A1 | 4/2009 | Krauss | |
| 2016/0128650 | A1* | 5/2016 | Wang | A61B 6/4241 378/5 |
| 2016/0206256 | A1* | 7/2016 | Berglund | G01T 1/2985 |
| 2016/0282476 | A1 | 9/2016 | Kappler et al. | |
| 2016/0307340 | A1 | 10/2016 | Allmendinger et al. | |
| 2017/0360385 | A1* | 12/2017 | Wang | A61B 6/4266 |
| 2019/0038244 | A1* | 2/2019 | Flohr | A61B 6/06 |
| 2019/0150864 | A1* | 5/2019 | Flohr | A61B 6/504 |

* cited by examiner

FIG 3

COMPUTED TOMOGRAPHY RECORDING WITH DIFFERENT SETS OF ENERGY THRESHOLDS

PRIORITY STATEMENT

The present application hereby claims priority under 35 U.S.C. § 119 to German patent application number DE 102017213479.8 filed Aug. 3, 2017, the entire contents of which are hereby incorporated herein by reference.

FIELD

At least one embodiment of the invention generally relates to a method, a computed tomography system, a computer program product and/or a computer-readable medium for recording a region of interest of an object to be examined with temporally different sets of energy thresholds.

BACKGROUND

Computed tomography is an imaging method used primarily for medical diagnosis and for the examination of material. In computed tomography, to record spatially three-dimensional image data, a radiation source, for example, an X-ray source and an X-ray detector interacting with said source rotate about an object to be examined. During the rotational movement, scan data is recorded within an angular sector. The projection scan data is a projection or a plurality of projections, which contain information about the attenuation of the radiation by the examination object from different projection angles. A two-dimensional image slice or a three-dimensional volume image of the examination object can be calculated from these projections. The projection scan data is also referred to as raw data or the projection scan data can be preprocessed so that, for example, detector-induced differences in attenuation intensity are reduced. Image data can then be reconstructed from this projection scan data, for example by way of so-called filtered back projection or by way of an iterative reconstruction method.

Numerous methods for scanning an examination object with a computed tomography system are known. For example, orbital scans, sequential orbital scans, with advance or spiral scans are employed. Other types of scan that are not based on orbital movements are also possible, such as scans with linear segments for example. Absorption data of the examination object is recorded from different imaging angles with the aid of at least one X-ray source and at least one X-ray detector lying opposite and this absorption data or projections collected in this way are computed into image slices through the examination object by way of corresponding reconstruction methods.

Computed tomography can use counting directly converting X-ray detectors. In directly converting X-ray detectors, the X-rays or the photons can be converted into electrical pulses by a suitable converter material. The converter material used can, for example, be CdTe, CZT, CdZnTeSe, CdTeSe, CdMnTe, InP, $TlBr_2$, $HgI_2$, GaAs or other materials. The electric pulses are evaluated by an evaluation electronics system, for example an integrated circuit (Application Specific Integrated Circuit, ASIC).

In counting X-ray detectors, incident X-rays are measured by counting the electric pulses which are triggered by the absorption of X-ray photons in the converter material. The level of the electric pulse is generally proportional to the energy of the absorbed X-ray photon. This enables spectral information to be extracted by comparing the level of the electric pulse with a threshold value. When energy-resolving or energy-selective counting X-ray detectors, for example directly converting X-ray detectors, are used, the measured datasets can be used as the basis for splitting material into two or three materials.

Publication DE 10 2015 205 301 A1 discloses a method for operating a counting digital X-ray image detector, wherein each pixel element and/or each pixel cluster is embodied as switchable between a first counting mode and a second counting mode that is different from the first.

Publication DE 10 2015 206 630 A1 discloses a multi-spectral imaging method, preferably a CT imaging method, wherein spectrally resolved projection scan data is acquired from a region to be imaged of an examination object and said data is assigned to a plurality of predetermined different partial spectra.

Publication DE 10 2007 046 514 A1 discloses a method and an image evaluation unit for recognizing and marking contrast agents in blood vessels of the lung with the aid of a CT examination using at least two different X-ray energy spectra. The method includes the following method steps:

scanning a patient at least in the region of the lung with two different X-ray energy spectra with the patient having contrast agents in the blood stream, reconstructing at least one two- or three-dimensional tomographic display for each X-ray energy spectrum, which reproduces the local spectrum-specific absorption properties of the scanned region, wherein a surrounding region is defined for a plurality of voxels for which an average ratio is calculated with the aid of the local absorption values of the at least two X-ray energy spectra, which specifies a measure for the ratio of the proportion of contrast agent to the proportion of soft tissue in the region surrounding the respective voxel under consideration, and, in the case of the ratio dropping below a prespecified threshold value, this voxel is considered to have reduced circulation and is marked in a tomographic display.

It is generally necessary to decide the fixed recording parameters, for example tube voltage, to be used for recording a region of interest of an object to be examined with a computed tomography system before starting the recording. Dynamic changes or adjustments to recording parameters are not made during the recording of a region of interest of an object to be examined with a computed tomography system. This enables larger regions to be used for recording a region of interest of an object to be examined with a computed tomography system with suboptimal recording parameters.

SUMMARY

Embodiments of the invention disclose a method, a computed tomography system, a computer program product and a computer-readable medium, which enable a region of interest of an object to be examined to be recorded with temporally different sets of energy thresholds.

Embodiments according to the invention are directed to a method, a computed tomography system, a computer program product and/or a computer-readable medium.

At least one embodiment of the invention relates to a method for recording a region of interest of an object to be examined with a computed tomography system comprising an energy-selective X-ray detector with a number of energy threshold values that can be set by way of a set of energy thresholds. The method comprises the first recording step, the setting step and second recording step. In the first recording step, first projection scan data is recorded with a first set of energy thresholds. In the setting step, a second set of energy thresholds different from the first set of energy thresholds is set based on a temporally variable parameter. In the second recording step, second projection scan data different from the first projection scan data is recorded with the second set of energy thresholds.

At least one embodiment of the invention further relates to a computed tomography system for carrying out an embodiment of the method, comprising a control unit and an X-ray detector. The control unit is designed to carry out the setting step and the potential presetting and determination steps. The control unit can carry out the steps based on the temporally variable parameter, the first projection scan data or a potential overview recording. The X-ray detector comprises settable energy threshold values. The X-ray detector in particular comprises a plurality of settable energy threshold values for each detection element or subpixel. The X-ray detector can further comprise a storage unit. The storage unit can store the first set of energy thresholds and/or the second set of energy thresholds. The X-ray detector can further be designed to carry out the method according to an embodiment of the invention, in particular when using a scanning parameter. Advantageously, the method according to an embodiment of the invention can be performed without examination-disrupting temporal delays inside a system.

At least one embodiment of the invention further relates a computer program product with a computer program, which can be loaded directly into a storage unit of a control unit of a computed tomography system with program sections in order to carry out the method according to at least one embodiment of the invention when the computer program is executed in the control unit of the computed tomography system.

At least one embodiment of the invention further relates to a computer-readable medium on which program sections that can be read-in and executed by a computing unit are stored in order to carry out the method according to at least one embodiment of the invention when the program sections are executed by the computing unit.

BRIEF DESCRIPTION OF THE DRAWINGS

The following explains example embodiments of the invention in more detail with reference to drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for recording a region of interest of an object to be examined with a computed tomography system comprising an energy-selective X-ray detector with a number of energy threshold values that can be set by way of a set of energy thresholds. The method comprises the first recording step, the setting step and second recording step. In the first recording step, first projection scan data is recorded with a first set of energy thresholds. In the setting step, a second set of energy thresholds different from the first set of energy thresholds is set based on a temporally variable parameter. In the second recording step, second projection scan data different from the first projection scan data is recorded with the second set of energy thresholds.

The X-ray detector used in the context of at least one embodiment of the invention can be called an energy-selective, (photon)-counting or directly converting X-ray detector. The X-ray detector comprises at least one detection element. The detection element comprises at least one energy threshold with an assigned energy threshold value. The detection element preferably comprises a plurality of energy thresholds each with an assigned energy threshold value. The energy threshold value can preferably be assigned as photon energy in keV. The energy threshold value can, for example, be set as photon energy, as voltage or as current. For example, the energy threshold value can be set in a comparator as a voltage value. The level of the electric pulse can, for example, compared with the voltage value in the comparator.

The energy threshold value can be given the designation $E_{i,n}$ or $E'_{i,n}$. The number of energy threshold values, in particular with respect to a detection element, can be an integer K, wherein $i \in [1; K]$. Herein, the number of the plurality of detection elements can be an integer N, wherein $n \in [1; N]$. The first set of energy thresholds includes, for example, the energy threshold value $E_{1,1}$, which is in particular assigned to one detection element (n=1). For example, the first set of energy thresholds includes a plurality of energy threshold values $E_{i,1}$, which are in particular assigned to one specific detection element (n=1). The first set of energy thresholds in particular includes a plurality of energy threshold values $E_{i,n}$, for example as a vector $\overrightarrow{E(E_{i,n})}$, which is assigned to a plurality of detection elements. Herein, in particular in each case a plurality of energy threshold values $E_{1,n}$ can be assigned in each case to one detection element, for example i=1, of the plurality of detection elements.

The second set of energy thresholds includes, for example, the energy threshold value $E'_{1,1}$, which is in particular assigned to one detection element (n=1). For example, the second set of energy thresholds includes a plurality of energy threshold values $E'_{i,1}$, which is in particular assigned to one specific detection element (n=1). In particular, the first set of energy thresholds includes a plurality of energy threshold values for example as a vector $\overrightarrow{E'(E_{i,n})}$, which is assigned to a plurality of detection elements. Herein, in particular in each case a plurality of energy threshold values $E'_{1,n}$ can be assigned in each case to one detection element, for example i=1, of the plurality of detection elements.

The energy threshold values $E_{i,n}$ or $E'_{i,n}$ of the plurality of detection elements can be selected as partially the same or different for the same i. The first set of energy thresholds and the second set of energy thresholds are at least partially different. The plurality of detection elements can, for example, be arranged in a matrix so that different detection elements have a spatially different position inside the X-ray detector.

The inventors have recognized that the optimum recording parameters for recording a region of interest of an object to be examined with a computed tomography system are in particular dependent upon the clinical issue in question, for example whether the examination or recording is performed with or without contrast agent, and in particular on the geometry of the patient. The inventors suggest that, during the (data) recording or during the CT scan, the configuration or the sets of energy thresholds of the X-ray detector are adapted dynamically to the requirements during the recording in order to achieve an optimum result. Advantageously, a fixed and invariant configuration with respect to the first set of energy thresholds and the second set of energy thresholds of the X-ray detector is avoided.

The second set of energy thresholds can be set as a function of a temporally variable parameter. The energy threshold values can be varied during the recording, i.e. between the first recording and the second recording. This enables the energy threshold values to be varied temporally. The temporally variable parameter changes during the recording. For example, the parameter can vary such that the first set of energy thresholds is less suitable or non-optimum for the second recording.

The settable number of energy threshold values can in particular represent a number of energy threshold values, wherein the energy threshold values are in particular each settable. The setting of an energy threshold value can include the loading of values, for example for adjusting a current or a voltage of a digital-analog converter. This enables an energy threshold value to be set. The setting of a set of energy thresholds can include the setting of a plurality of energy threshold values.

The first projection scan data is different from the second projection scan data. The first projection scan data differs at least in that the second projection scan data is recorded with a second set of energy thresholds different from the first set of energy thresholds. The first projection scan data can further differ from the second projection scan data in that the first projection scan data is recorded under a first projection angle and the second projection scan data is recorded under a projection angle different from the first projection angle. This, for example, enables at least partially different projections to be recorded in the steps of the first recording and the second recording of the region of interest.

According to one embodiment of the invention, the method further comprises the presetting step. In the presetting step, the first set of energy thresholds is based on the temporally variable parameter. The first set of energy thresholds can, for example, be set based on a predetermined value of the temporally variable parameter. The predetermined value can, for example, be defined based on previous recordings. The predetermined value can be an expected value. The predetermined value can be any value. The predetermined value can assume a value typical of a type of examination. Advantageously, a more optimal first set of energy thresholds can also be selected for the recording. Advantageously, it is possible to avoid a uniform or constant set of energy thresholds. Advantageously, the first set of energy thresholds can be adapted to the recording of the first projection scan data or the second set of energy thresholds to the recording of the second projection scan data. The first set of energy thresholds can, for example, be selected or determined based on a topogram, i.e. an overview recording.

According to one embodiment of the invention, the method further comprises the determination step. In the determination step, the second set of energy thresholds is determined based on the first projection scan data and/or the temporally variable parameter. Advantageously, the second set of energy thresholds can be set based on the first projection scan data; for example, it is possible to predict or determine an optimal second set of energy thresholds. Knowledge of the first projection scan data can be used to determine or extrapolate the temporally variable parameter.

The potential overview recording can be used as the basis for determining the temporally variable parameter for different time points or successive recording steps. The overview recording or the first projection scan data can, for example, indicate the attenuation or geometry of the object or the patient. For example, the attenuation or geometry can be determined along the axis of rotation z. The first recording can be performed at a different z-position than the second recording so that the different z-position enables the first recording to be assigned a first time point and the second recording a second time point. Knowledge of the attenuation or geometry of the object can be used to determine the temporally variable parameter, for example the attenuation or extension of the object along the axis of rotation. Higher attenuation can result in fewer counting events in the X-ray detector and, in particular simultaneously, changed energy distribution of the X-rays incident on the X-ray detector following penetration of the object. Advantageously, the second set of energy thresholds can be adapted to the number of expected counting events and/or to the expected energy distribution.

The first projection scan data can be used as the basis for the determination of the temporally variable parameter for different time points or successive recording steps. The first projection scan data can, for example, indicate the attenuation or geometry of the object or the patient. For example, the attenuation or geometry in the x-y plane can be determined perpendicular to the axis of rotation z. The first recording can be performed under a different projection angle, which is indicated by way of the angle of rotation, from the second recording so that the different projection angle enables a first time point to be assigned to the first recording and a second time point to the second recording. Knowledge of the attenuation or geometry of the object enables the temporally variable parameter, for example the attenuation or extension of the object along of the angle of rotation in the x-y plane about the axis of rotation, to be determined. Advantageously, the second set of energy thresholds can be adapted to the number of expected counting events and/or to the expected energy distribution.

According to one embodiment of the invention, the temporally variable parameter is an object parameter, a scanning parameter, a detector parameter or an X-ray source parameter. The object parameter can, for example, be attenuation, geometry, extension, weight, an anatomical property or the like. The object parameter is assigned to the examination object. The scanning parameter can indicate the, in particular temporal, course of a scanning pattern. The detector parameter can include properties of the detector, for example a time-dependent polarization state, a time-dependent offset, a time-dependent amplification factor, an extension or a spatial arrangement of a plurality of detection elements with respect to one another. The X-ray source parameter can in particular include temporally variable settings regarding X-ray generation or the provision of an, in particular temporally variable, X-ray beam suitable for the recording. Advantageously, the second set of energy thresholds can be adapted to temporal variations in the examination object, the X-ray detector or the X-ray source or to a temporally variable scanning pattern.

According to one embodiment of the invention, the object parameter includes an attenuation property, a geometry property or an anatomical property of the examination object. The temporally variable parameter, in particular as an object parameter, can vary along the direction of rotation around the examination object or along the axis of rotation. Typically, successive recordings are recorded along a circular or helical trajectory. Herein, in particular the thickness of the examination object to be penetrated by the X-rays can vary along its circumference or the direction of rotation. Further, the circumference of the examination object can vary along the axis of rotation.

The geometry property can indicate the thickness or the path length through the examination object to be penetrated. The geometry property can indicate the circumference of the examination object. The geometry property can indicate the shape, for example the cross-sectional area or the outer edges of the cross-sectional area for example along an area perpendicular to the axis of rotation or the outline of the examination object in an area parallel to the patient bench.

The attenuation property can indicate a density or an absorption coefficient. The attenuation property can include the geometry property enabling an attenuation property to be determined from the geometry and, for example, the density or the absorption coefficient.

The anatomical property can enable conclusions to be drawn regarding the geometry property or the attenuation property. The anatomical property can include a body region, an organ, a muscle, a bone or other anatomical features. For example, the first set of energy thresholds or the second set of energy thresholds and potentially the spatial resolution can be adapted to the anatomical property. For example, a higher spatial resolution can be set on the X-ray detector in the region of the depiction of the heart on the X-ray detector. For example, in the region of the depiction of the heart on the X-ray detector, the energy threshold values can be set differently from the energy threshold values in the region outside the depiction of the heart. The anatomical property can, for example, be predetermined based on the type of recording, for example cardio recording. Advantageously, the recording can be adapted to the examination object. Advantageously, the recording can be optimized for the examination object or the type of recording.

According to one embodiment of the invention, the scanning parameter is a periodic function. For example, the first recording and the second recording can be part of a series of recording steps with alternating or periodic sets of energy thresholds. The periodic sequence of the first set of energy thresholds and of the second set of energy thresholds or energy threshold values thereof can be varied along the direction of rotation or movement.

In particular in the case of the multiple succession of, for example, in alternation a recording and a second recording, a first set of energy thresholds and second set of energy thresholds can be selected such that higher energy scanning takes place. The energy threshold values of the first set of energy thresholds and the energy threshold values of the second set of energy thresholds can be at least partially different so that the examination object can be scanned with a higher number of energy threshold values than the number of energy threshold values of an individual set of energy thresholds.

The energy threshold values or the sets of energy thresholds can be varied periodically during the rotation so that data for different energies or energy threshold values is acquired with different scanning patterns, wherein the number of acquired energies exceeds the number of settable energy threshold values for each detection element in a set of energy thresholds. It advantageously possible to achieve higher energy resolution.

According to one embodiment of the invention, third projection scan data is formed as a function of the first projection scan data and the second projection scan data. In the case of recording including a periodic scanning parameter it is, for example, possible for third projection scan data to be formed, wherein all the events of the first projection scan data and the second projection scan data are included and the count values of the third projection scan data are assigned to a higher number of energy threshold values than the number of energy threshold values in an individual set of energy thresholds.

For example, the count values can be assigned on the basis of probabilities to the higher number of energy threshold values; this can in particular be applied to two adjacent or overlapping energy ranges of an energy threshold value of the first set of energy thresholds and an energy threshold value of the second set of energy thresholds different therefrom. It is advantageously possible to achieve higher energy resolution in the recording. Advantageously, the region of interest can be scanned with a higher number of energy threshold values. The first set of energy thresholds and the second set of energy thresholds can be used to form a common third set of energy thresholds, which, for example, contains all the energy threshold values of the first set of energy thresholds and the second set of energy thresholds.

According to one embodiment of the invention, the X-ray detector comprises a plurality of detection elements and the temporally variable parameter is a function of a spatial arrangement of the detection elements inside the X-ray detector. The detector parameter can be a function of a spatial dependence inside a detection surface of the X-ray detector. The energy threshold values of the first set of energy thresholds or the energy threshold values of the second set of energy thresholds can be at least partially different along a detection surface of the X-ray detector. The energy threshold values inside a set of energy thresholds can be set differently for individual detection elements inside the X-ray detector. For example, the energy threshold values in the central region of the X-ray detector or with small fan angles of the incident X-ray fan or cone can be set differently from peripheral regions of the X-ray detector or with comparatively larger fan angles. It is advantageously possible to compensate effects from a different degree of absorption along the detection surface, for example due to the geometry of the examination object.

According to one embodiment of the invention, the X-ray source parameter includes a tube current, a tube voltage, filtration or collimation. The first set of energy thresholds or the second set of energy thresholds and a potentially variable spatial resolution of the X-ray detector can be set as a function of an X-ray source parameter. For example, the first set of energy thresholds or the second set of energy thresholds and a potentially variable spatial resolution of the X-ray detector can be set by way of a coupling or as a function of automatic tube current modulation. The automatic tube current modulation can, for example, be a function of a geometry property of the examination object. Advantageously, the recording can be adapted to the photon flux.

According to one embodiment of the invention, for the first set of energy thresholds, the X-ray detector has a spatial resolution different from the second set of energy thresholds. A detection element of the X-ray detector can be divided into subpixels. This enables the spatial resolution of the X-ray detector to be set. The detection element can have a plurality of subpixels in a matrix arrangement. The detection element can, for example, have 2×2, 4×4 or 4×6 subpixels. A plurality of subpixels can be combined by so-called binning to form one detection unit; herein all the count values of the plurality of subpixels can be combined to form one single count value of the plurality of subpixels for each energy threshold value. Advantageously, the spatial resolution can be increased for particularly interesting regions of the examination object. Advantageously, the data volume can be reduced for less interesting regions of the examination object. Binning within a set of energy thresholds can be different for different energy threshold values.

At least one embodiment of the invention further relates to a computed tomography system for carrying out an embodiment of the method, comprising a control unit and an X-ray detector. The control unit is designed to carry out the setting step and the potential presetting and determination steps. The control unit can carry out the steps based on the temporally variable parameter, the first projection scan data or a potential overview recording. The X-ray detector comprises settable energy threshold values. The X-ray detector in particular comprises a plurality of settable energy threshold values for each detection element or subpixel. The X-ray detector can further comprise a storage unit. The storage unit can store the first set of energy thresholds and/or the second set of energy thresholds. The X-ray detector can further be designed to carry out the method according to an embodiment of the invention, in particular when using a scanning parameter. Advantageously, the method according to an embodiment of the invention can be performed without examination-disrupting temporal delays inside a system.

At least one embodiment of the invention further relates a computer program product with a computer program, which can be loaded directly into a storage unit of a control unit of a computed tomography system with program sections in order to carry out the method according to at least one embodiment of the invention when the computer program is executed in the control unit of the computed tomography system.

At least one embodiment of the invention further relates to a computer-readable medium on which program sections that can be read-in and executed by a computing unit are stored in order to carry out the method according to at least one embodiment of the invention when the program sections are executed by the computing unit.

Figure 1:
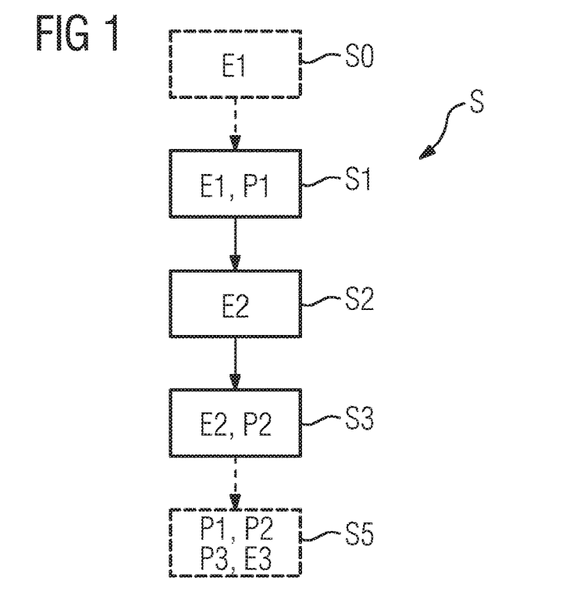
FIG. 1 shows a schematic representation of the method according to the invention according to a first embodiment.

FIG. 1 shows an example embodiment of the method S according to the invention in a first embodiment. The method S for recording a region of interest of an examination object with a computed tomography system comprising an energy-selective X-ray detector with number of energy threshold values that can be set by way of a set of energy thresholds E1, E2 comprises the first recording step S1, the setting step S2 and the second recording step S3. In the first recording step S1, first projection scan data P1 is recorded with a first set of energy thresholds E1. In the setting step S2, a second set of energy thresholds E2 different from the first set of energy thresholds E1 is set based on a temporally variable parameter. In the second recording step S3, second projection scan data P2 different from the first projection scan data P1 is recorded with the second set of energy thresholds E2.

The X-ray detector used in the context of an embodiment of the invention is designated an energy-selective, (photon)-counting or direct-converting X-ray detector. The X-ray detector comprises at least one detection element. The detection element comprises at least one energy threshold with an assigned energy threshold value. The detection element preferably comprises a plurality of energy thresholds each with an assigned energy threshold value. The energy threshold value can preferably be assigned to a photon energy in keV. The energy threshold value is, for example, set as photon energy, as voltage or as current. For example, the energy threshold value is set in a comparator as a voltage value. The level of the electric pulse can, for example, be compared to the voltage value in the comparator.

The energy threshold value can be given the designation $E_{i,n}$ or $E'_{i,n}$. The number of energy threshold values, in particular with respect to a detection element, is an integer K, wherein $i \in [1; K]$. Herein, the number of plurality of detection elements can be an integer N, wherein $n \in [1; N]$. The first set of energy thresholds E1 includes, for example, the energy threshold value $E_{1,1}$, which is in particular assigned to one detection element (n=1). For example, the first set of energy thresholds E1 includes a plurality of energy threshold values $E_{i,1}$, which are in particular assigned to one specific detection element (n=1). In particular, the first set of energy thresholds E1 includes a plurality of energy threshold values $E_{i,n}$, for example as a vector $\overrightarrow{E(E_{i,n})}$, which are assigned to a plurality of detection elements. Herein, in particular in each case a plurality of energy threshold values $E_{1,n}$ can be assigned in each case to one detection element, for example i=1, of the plurality of detection elements.

The second set of energy thresholds E2 includes for example the energy threshold value $E'_{1,1}$, which is in particular assigned to one detection element (n=1). For example, the second set of energy thresholds E2 includes a plurality of energy threshold values $E'_{i,1}$, which is in particular assigned to one specific detection element (n=1). In particular, the first set of energy thresholds E2 includes a plurality of energy threshold values $E'_{i,n}$, for example as a vector $\overrightarrow{E'(E_{i,n})}$, which is assigned to a plurality of detection elements. Herein, in particular in each case a plurality of energy threshold values $E'_{1,n}$ can be assigned in each case to one detection element, for example i=1, of the plurality of detection elements.

The energy threshold values $E_{i,n}$ or $E'_{i,n}$ of the plurality of detection elements can be selected as partially the same or different for the same i. The first set of energy thresholds E1 and the second set of energy thresholds E2 are at least partially different. The plurality of detection elements is, for example, arranged in a matrix so that different detection elements have a spatially different position inside the X-ray detector.

The second set of energy thresholds E2 can be set as a function of a temporally variable parameter. The energy threshold values can be varied during the recording, i.e. between the first recording S1 and the second recording S3. This enables can the energy threshold values to be varied temporally. The temporally variable parameter changes during the recording. For example, the temporally variable parameter can be varied such that the first set of energy thresholds E1 is less suitable or non-optimum for the second recording S3.

The settable number of energy threshold values can in particular represent a number of energy threshold values, wherein the energy threshold values are each settable. The setting S2 of an energy threshold value can include the loading of values for example for setting a current or a voltage of a digital-analog converter. This enables an energy threshold value to be set. The setting S2 of a set of energy thresholds can include the setting of a plurality of energy threshold values.

The first projection scan data P1 is different from the second projection scan data P2. The first projection scan data P1 differs at least in that the second projection scan data P2 is recorded with a second set of energy thresholds E2 different from the first set of energy thresholds E1. The first projection scan data P1 can further differ from the second projection scan data P2 in that the first projection scan data P1 is recorded under a first projection angle and the second projection scan data P2 is recorded under a projection angle different from the first projection angle different projection angle. This, for example, enables at least partially different projections to be recorded in the steps of the first recording S1 and the second recording S3 of the region of interest.

The method S can further include the step S0 of the presetting of the first set of energy thresholds E1 based on the temporally variable parameter. In the presetting step S0, the first set of energy thresholds E1 is preset based on the temporally variable parameter. The first set of energy thresholds E1 can, for example, be based on a predetermined value of the temporally variable parameters. The predetermined value can, for example, be based on previous recordings. The predetermined value can be an expected value. The predetermined value can be any value. The predetermined value can assume a value typical of a type of examination. The first set of energy thresholds E1 can, for example, be selected or determined based on a topogram, i.e. an overview recording of the region of interest.

The temporally variable parameter can be an object parameter, a scanning parameter, a detector parameter or an X-ray source parameter. The object parameter can, for example, be attenuation, geometry, extension, weight, an anatomical property or the like. The object parameter is assigned to examination object. The scanning parameter can indicate the, in particular temporal, course of a scanning pattern. The detector parameter can include properties of the detector, for example a time-dependent polarization state, a time-dependent offset, a time-dependent amplification factor, an extension or a spatial arrangement of a plurality of detection elements with respect to one another. The X-ray source parameter can in particular include temporally settings regarding X-ray generation or the provision of an, in particular temporally variable, X-ray beam suitable for the recording.

The object parameter can include an attenuation property, a geometry property or an anatomical property of the examination object. The temporally variable parameter, in particular as an object parameter, can vary along the direction of rotation around the examination object or along the axis of rotation. Typically, successive recordings are recorded along a circular or helical trajectory. Herein, in particular the thickness of the examination objected to be penetrated by the X-rays can vary along its circumference or the direction of rotation. Further, the circumference of the examination object can vary along the axis of rotation.

The geometry property can indicate the thickness or the path length through the examination object to be penetrated. The geometry property can indicate the circumference of the examination object. The geometry property can indicate the shape, for example the cross-sectional area or the outer edges, of the cross-sectional area for example along an area perpendicular to the axis of rotation or the outline of the examination object in an area parallel to the patient bench.

The attenuation property can indicate a density or an absorption coefficient. The attenuation property can include the geometry property so that an attenuation property can be determined from the geometry and, for example, the density or the absorption coefficient.

The anatomical property can enable conclusions to be drawn regarding the geometry property or the attenuation property. The anatomical property can include a body region, an organ, a muscle, a bone or other anatomical features. For example, the first set of energy thresholds or the second set of energy thresholds and possibly the spatial resolution can be adapted to the anatomical property. For example, a higher spatial resolution can be set on the X-ray detector in the region of the depiction of the heart on the X-ray detector. For example, in the region of the depiction of the heart on the X-ray detector, the energy threshold values can be set differently from the energy threshold values in the region outside the depiction of the heart. The anatomical property can, for example, be predetermined based on the type of recording, for example cardio recording.

The scanning parameter can be a periodic function. For example, the first recording S1 and the second recording S3 can be part of a series of recording steps with alternating or periodic sets of energy thresholds. In particular, in the case of the multiple succession of, in alternation, a first recording S1 and second recording S3, a first set of energy thresholds E1 and second set of energy thresholds E2 can be selected such that higher energy scanning takes place. The energy threshold values of the first set of energy thresholds E1 and the energy threshold values of the second set of energy thresholds E2 can be selected as at least partially different so that the examination object can be scanned with a higher number of energy threshold values than the number of energy threshold values of an individual set of energy thresholds E1, E2. The energy threshold values or the sets of energy thresholds E1, E2 can varied periodically during the rotation so that data with different energies or energy threshold values are acquired with different scanning patterns, wherein the number of acquired energies exceeds the number of settable energy threshold values for each detection element in a set of energy thresholds E1, E2.

The method S can further include the step of merging S5 of first projection scan data P1 and second projection scan data P2 to form third projection scan data P3. The third projection scan data P3 can be formed as a function of the first projection scan data P1 and the second projection scan data P2.

In particular in the case of a recording including a periodic scanning parameter it is, for example, possible for third projection scan data P3 to be formed. All events of the first projection scan data P1 and the second projection scan data P2 can be included in the third projection scan data P3 and the count values of the third projection scan data P3 can be assigned a higher number of energy threshold values than the number of energy threshold values in an individual set of energy thresholds E1, E2. For example, the count values can be assigned on the basis of probabilities to the higher number of energy threshold values; this can in particular be applied to two adjacent or overlapping energy ranges of an energy threshold value of the first set of energy thresholds E1 and a different energy threshold value of the second set of energy thresholds E2 different therefrom. The first set of energy thresholds E1 and the second set of energy thresholds E2 can be used to form a common third set of energy thresholds E3, which, for example, contains all the energy threshold values of the first set of energy thresholds E1 and the second set of energy thresholds E2.

The X-ray detector preferably comprises a plurality of detection elements. The temporally variable parameter can be a function of a spatial arrangement of the detection elements inside the X-ray detector. The detector parameter can be a function of a spatial dependence inside a detection surface of the X-ray detector. The energy threshold values of the first set of energy thresholds E1 or the energy threshold values of the second set of energy thresholds E2 can be at least partially different along a detection surface of the X-ray detector. The energy threshold values inside a set of energy thresholds E1, E2 can be set differently for individual detection elements inside the X-ray detector. For example, the energy threshold values in the central region of the X-ray detector or with small fan angles of the incident X-ray fan or cone can be set differently from peripheral regions of the X-ray detector or with comparatively larger fan angles.

The X-ray source parameter can be a tube current, a tube voltage, filtration or collimation. The first set of energy thresholds E1 or the second set of energy thresholds E2 and a possibly variable spatial resolution of the X-ray detector can be set as a function of an X-ray source parameter. For example, the first set of energy thresholds E1 or the second set of energy thresholds E2 and a possibly variable spatial resolution of the X-ray detector can be set by way of a coupling or as a function of automatic tube current modulation. The automatic tube current modulation can, for example, be a function of a geometry property of the examination object.

For the first set of energy thresholds E1, the X-ray detector can have a spatial resolution different from the second set of energy thresholds E2. A detection element of the X-ray detector can be divided into subpixels. This enables the spatial resolution of the X-ray detector to be set. The detection element can, for example, have a plurality of subpixels in a matrix arrangement. The detection element can, for example, have 2×2, 4×4 or 4×6 subpixels. A plurality of subpixels can be combined by so-called binning to form a detection unit; herein all the count values of the plurality of subpixels can be combined to form one single count value of the plurality of subpixels for each energy threshold value. Binning within a set of energy thresholds can be different for different energy threshold values.

Figure 2:
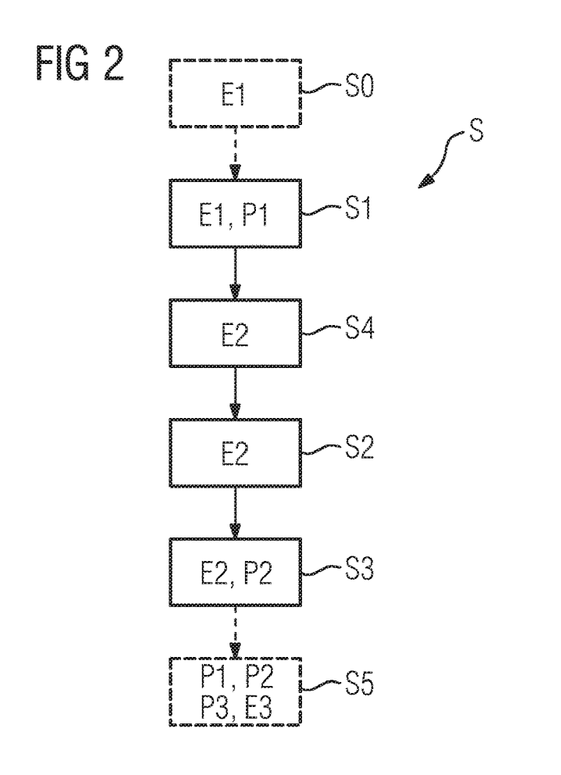
FIG. 2 shows a schematic representation of the method according to the invention according to a second embodiment.

FIG. 2 shows an example embodiment of the method according to the invention S in a second embodiment. The method can further comprise the determination step S4. In the determination step S4, the second set of energy thresholds E2 is determined based on the first projection scan data P1 and/or the temporally variable parameter. Knowledge of the first projection scan data P1 can be used to determine or extrapolate the temporally variable parameter.

The potential overview recording can be used as the basis for determining the temporally variable parameter for different time points or successive recording steps S1, S3. The overview recording or the first projection scan data P1 can, for example, indicate the attenuation or geometry of the object or the patient. For example, the attenuation or geometry can be determined along the axis of rotation z. The first recording S1 can be performed at a different z-position than the second recording S3 so that the different z-position enables the first recording S1 to be assigned a first time point and the second recording S3 a second time point. Knowledge of the attenuation or geometry of the object can be used to determine the temporally variable parameter, for example the attenuation or extension of the object along the axis of rotation. Higher attenuation can result in fewer counting events in the X-ray detector and, in particular simultaneously, changed energy distribution of the X-rays incident on the X-ray detector following penetration of the object.

The first projection scan data P1 can be used as the basis for determining the temporally variable parameter for different time points or the following recording step S2. The first projection scan data P1 can, for example, indicate the attenuation or geometry of the object or the patient. For example, the attenuation or geometry in the x-y plane can be determined perpendicular to the axis of rotation z. The first recording S1 can be performed under a different projection angle, which is indicated by way of the angle of rotation, than the second recording S3 so that the different projection angle enables a first time point to be assigned to the first recording S1 and a second time point to the second recording S3. Knowledge of the attenuation or geometry of the object can be used to determine the temporally variable parameter, for example the attenuation or extension of the object along of the angle of rotation in the x-y plane about the axis of rotation.

Figure 3:
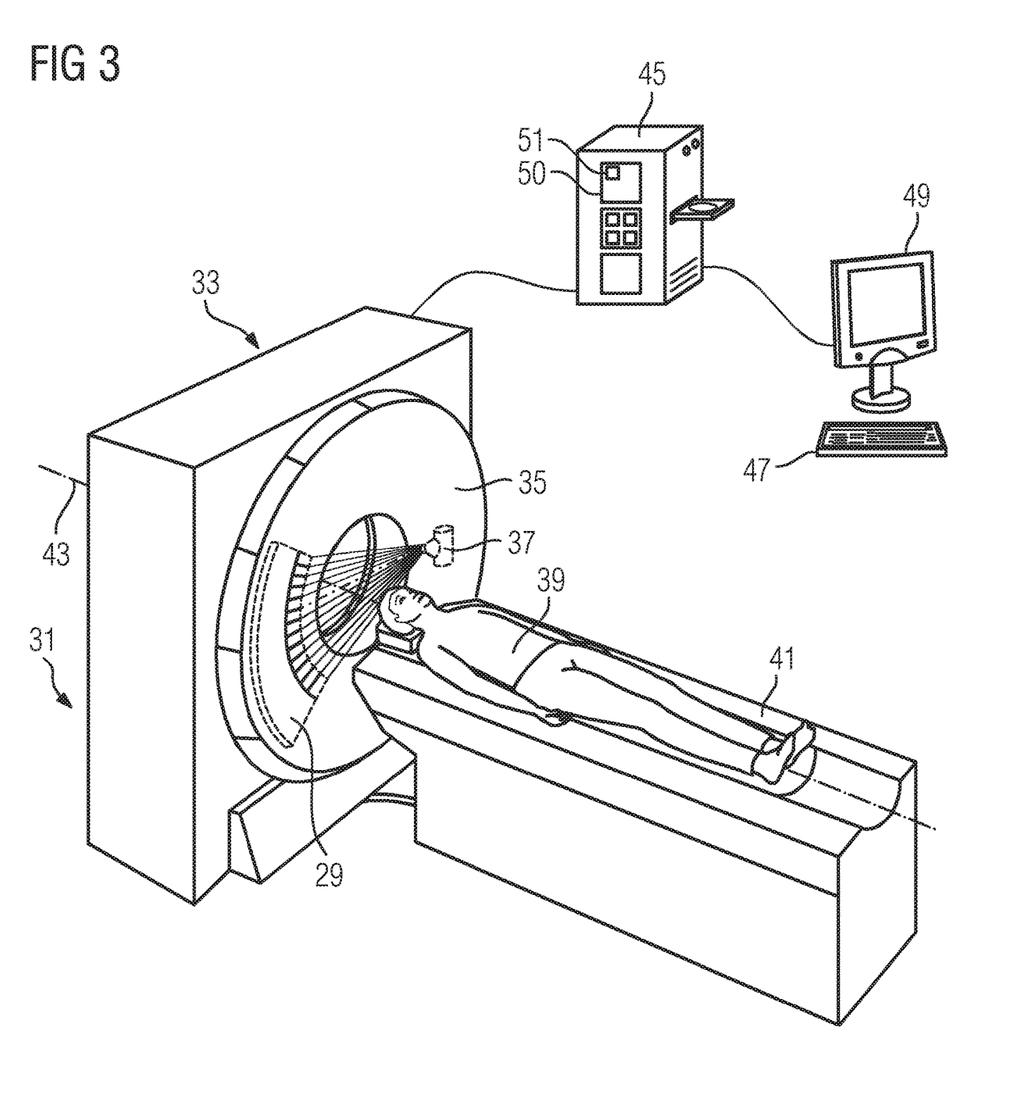
FIG. 3 shows a schematic representation of the computed tomography system according to an embodiment of the invention.

FIG. 3 shows an example embodiment of the computed tomography system according to an embodiment of the invention 31 for carrying out the method according to an embodiment of the invention. The computed tomography system 31 contains a projection-data-recording unit 33 with a rotor 35. The rotor 35 comprises an X-ray source 37 and the X-ray detector 29. The examination object 39 is supported on the patient bench 41 and can be moved along the axis of rotation z 43 through the projection-data-recording unit 33. A computing unit 45 is used to control and calculate the image slices. The computing unit 45 comprises a control unit 50 with a storage unit 51. An input unit 47 and an output unit 49 are connected to the computing unit 45.

The computer program product includes a computer program, which can be loaded directly into a storage unit 51 of the control unit 50 of the computed tomography system 31, with program sections in order to carry out all the steps of the method according to an embodiment of the invention when the computer program is executed in the control unit 50 of the computed tomography system 31. The computer-readable medium is used to store program sections that can be read-in and executed by a computing unit 45 in order to carry out all the steps of the method according to an embodiment of the invention when the program sections are executed by the computing unit 45.

The control unit 50 is designed to carry out the setting step, the potential presetting step and the potential determination step. The control unit 50 can carry out the steps based on the temporally variable parameter, the first projection scan data or a potential overview recording. The storage unit 51 can be used to store the first set of energy thresholds and/or the second set of energy thresholds.

The X-ray detector 29 has settable energy threshold values. The X-ray detector 29 in particular has a plurality of settable energy threshold values for each detection element or subpixel. The X-ray detector 29 can further comprise a storage unit. The X-ray detector 29 can further be designed to carry out the method according to an embodiment of the invention, in particular when using a scanning parameter.

Although the invention was illustrated in more detail by the preferred example embodiment, the invention is not restricted by the disclosed examples and other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for recording a region of interest of an examination object with a computed tomography system, including an energy-selective X-ray detector including a number of energy threshold values settable via a set of energy thresholds, the method comprising:
   recording first projection scan data with a first set of energy thresholds;
   setting a second set of energy thresholds, different from the first set of energy thresholds, based on a temporally variable parameter; and
   recording second projection scan data, different from the first projection scan data, with the second set of energy thresholds.

2. The method of claim 1, further comprising:
   presetting the first set of energy thresholds based on the temporally variable parameter.

3. The method of claim 2, further comprising:
   determining the second set of energy thresholds based on at least one of the first projection scan data and the temporally variable parameter.

4. The method of claim 2, wherein the temporally variable parameter is an object parameter, a scanning parameter, a detector parameter or an X-ray source parameter.

5. The method of claim 1, further comprising:
   determining the second set of energy thresholds based on at least one of the first projection scan data and the temporally variable parameter.

6. The method of claim 1, wherein the temporally variable parameter is an object parameter, a scanning parameter, a detector parameter or an X-ray source parameter.

7. The method of claim 6, wherein the object parameter includes an attenuation property, a geometry property or an anatomical property of the examination object.

8. The method of claim 6, wherein the scanning parameter includes a periodic dependence.

9. The method of claim 8, wherein third projection scan data is formed as a function of the first projection scan data and the second projection scan data.

10. The method of claim 6, wherein the energy-selective X-ray detector comprises a plurality of detection elements and wherein the temporally variable parameter is a function of a spatial arrangement of the plurality of detection elements inside the energy-selective X-ray detector.

11. The method of claim 6, wherein the X-ray source parameter includes a tube current, a tube voltage, filtration or collimation.

12. The method of claim 1, wherein, for the first set of energy thresholds, the energy-selective X-ray detector includes a spatial resolution different from the second set of energy thresholds.

13. A non-transitory computer program product storing a computer program, directly loadable into a memory of a controller of a computed tomography system, the computer program including program sections for carrying out the method of claim 1 when the computer program is executed in the controller of the computed tomography system.

14. A non-transitory computer-readable medium storing program sections, readable-in and executable by a computer to carry out the method of claim 1 when the program sections are executed by the computer.

15. The method of claim 1, wherein the first set of energy thresholds are initially set based on the temporally variable parameter.

16. The method of claim 15, further comprising:
determining the second set of energy thresholds based on at least one of the first projection scan data and the temporally variable parameter.

17. The method of claim 15, wherein the temporally variable parameter is an object parameter, a scanning parameter, a detector parameter or an X-ray source parameter.

18. A computed tomography system, comprising:
an energy-selective X-ray detector including a number of energy threshold values settable via a first set of energy thresholds and a second set of energy thresholds; and
a controller, the controller being configured to
record first projection scan data with the first set of energy thresholds,
set the second set of energy thresholds, different from the first set of energy thresholds, based on a temporally variable parameter, and
record second projection scan data, different from the first projection scan data, with the second set of energy thresholds.

19. The computed tomography system of claim 18, wherein the first set of energy thresholds are set based on the temporally variable parameter.

20. The computed tomography system of claim 18, wherein the controller is further configured to determine the second set of energy thresholds based on at least one of the first projection scan data and the temporally variable parameter.

* * * * *